United States Patent [19]

Stock et al.

[11] 4,157,475
[45] Jun. 5, 1979

[54] ELECTRON ACCELERATOR COMPRISING A TARGET EXPOSED TO THE ELECTRON BEAM

[75] Inventors: Eberhard Stock, Erlangen, Fed. Rep. of Germany; Leonhard Taumann, Walnut Creek, Calif.

[73] Assignee: Applied Radiation Corporation, Walnut Creek, Calif.

[21] Appl. No.: 863,514

[22] Filed: Dec. 22, 1977

[30] Foreign Application Priority Data

Oct. 21, 1977 [CA] Canada ................................ 289258

[51] Int. Cl.² .............................................. H01J 35/00
[52] U.S. Cl. ..................................... 250/503; 250/398; 250/505
[58] Field of Search ............... 250/505, 511, 512, 513, 250/493, 503, 398, 490; 313/2, 55, 59, 326

[56] References Cited

U.S. PATENT DOCUMENTS

| 2,844,736 | 7/1958 | Johns et al. | 250/512 |
| 3,040,175 | 6/1962 | Kern | 250/505 |
| 3,227,880 | 1/1966 | Wideröe | 250/505 |
| 3,969,629 | 7/1976 | McIntyre | 250/503 |
| 3,992,633 | 11/1976 | Braun et al. | 250/505 |

FOREIGN PATENT DOCUMENTS 351651  6/1935  Fed. Rep. of Germany ........... 250/505

Primary Examiner—Bruce C. Anderson
Attorney, Agent, or Firm—Hill, Gross, Simpson, Van Santen, Steadman, Chiara & Simpson

[57] ABSTRACT

In order to supply a dose rate which is as constant as possible over the cross section of the x-ray cone for radiation therapy, especially at lesser tissue depths (e.g. 3 cm), the surfaces of the collimator which define the margin of the x-ray cone are roughened for example by means of grooves transverse to the radiation direction, the grooves having semicircular or step-shaped cross sectional configuration, and advantageously being formed in a thin walled sleeve of low atomic number.

6 Claims, 5 Drawing Figures

ELECTRON ACCELERATOR COMPRISING A TARGET EXPOSED TO THE ELECTRON BEAM

BACKGROUND OF THE INVENTION

The invention relates to an electron accelerator comprising a target exposed to the electron beam for the purpose of producing x-ray bremsstrahlung, with a conical compensating member arranged in a centered fashion in the x-ray cone, as well with a collimator limiting (or defining) the x-ray cone.

The x-ray cone issuing from electron accelerators which are used in radiation therapy is to have a dose rate of equal magnitude over its entire cross-section. This is necessary in order to be able to apply the minimum dose required for destroying the diseased tissue in the region of the seat (or nidus) of the disease, and, at the same time, to be able to spare, insofar as possible, the adjacent healthy tissue.

In the case of electron accelerators wherein x-ray bremsstrahlung is produced in a so-called target through declaration of the electrons, the dose rate in the x-ray cone being issued has a conical characteristic with a maximum in the direction in which the electron beam impinges upon the target. This maximum most often coincides with the symmetry axis of the collimator. It is known to compensate the dose rate in the x-ray cone defined (or diaphrammed-out) by the collimator by installing a compensating member in the x-ray cone. Said compensating member has a conical construction. It is adapted in its form and in its radiation absorption properties to the characteristic of the dose rate at its point of application. In the case of electron accelerators provided with a compensating member in the aforementioned manner, an x-ray cone is issued whose dose rate is of equal magnitude at a fixed tissue depth (generally 10 cm) over the entire cross-section of the x-ray cone. At a lesser tissue depth, the dose rate, as illustrated in FIG. 2 with the drawn-out (or extended) solid line curve, increases from the interior toward the exterior. This can lead to a non-uniform dose distribution in the seat of the tumor or it can lead to a greater dose charge (or burden) on the healthy tissue.

SUMMARY OF THE INVENTION

The object which is the basis of the invention consists in compensating the dose rate of the x-ray cone issuing from an electron accelerator in such a manner that the undesired excessive increase in the dose rate in the marginal region of the x-ray cone can be avoided at a lesser tissue depth.

Accordingly, in the case of an electron accelerator of the type initially cited, the invention specifies that the interior wall surfaces of the collimator which limit (or define) the x-ray cone, he roughened-up in a direction transverse to the radiation direction. The realization underlying this solution is that the atoms of the internal walls of the collimator which define the x-ray cone; i.e., the internal walls of the collimator shielding block as well as the respective frontal (or leading) edges or inner wall surfaces of the adjustable x-ray shielding plates (said frontal edges limiting the x-ray cone), scatter the x-rays at their atomic lattice. The probable cause of the excessive increase in the dose rate in the marginal region of the x-ray cone at a minimal (or low) tissue depth is the superposition of the scattered component with the otherwise compensated x-ray cone. Since the forward scattering very strongly predominates in the case of energies of several MeV; i.e., the dose rate of the scattered component strongly decreases with the angle of scattering, scattering-in is decreased by roughening up the walls.

In a particularly advantageous embodiment of the invention, semicircular grooves may be admitted into the interior wall surfaces of the collimator which limit the x-ray cone, said semicircular grooves being arranged transversely to the radiation direction. Semicircular grooves of this type can be turned or milled, respectively, with relative ease into the conical recess of the shielding block of the collimator and into the frontal edges of the x-ray shielding plates. In this fashion, a large portion of the radiation quanta scattered in a small angle is absorbed in the edges of the grooves.

Particularly favorable results are also obtained if, in an expedient further development of the invention, stepped grooves are introduced transversely to the radiation direction in the interior wall surfaces of the collimator. Due to these stepped grooves, there is a displacement of scatter locations to greater depths of the material. The quanta scattered at an acute angle are strongly absorbed in the edges of the grooves.

Other objects, features and advantages of the invention will be apparent from the following detailed description taken in connection with the accompanying sheet of drawings.

DETAILED DESCRIPTION

Figure 1:
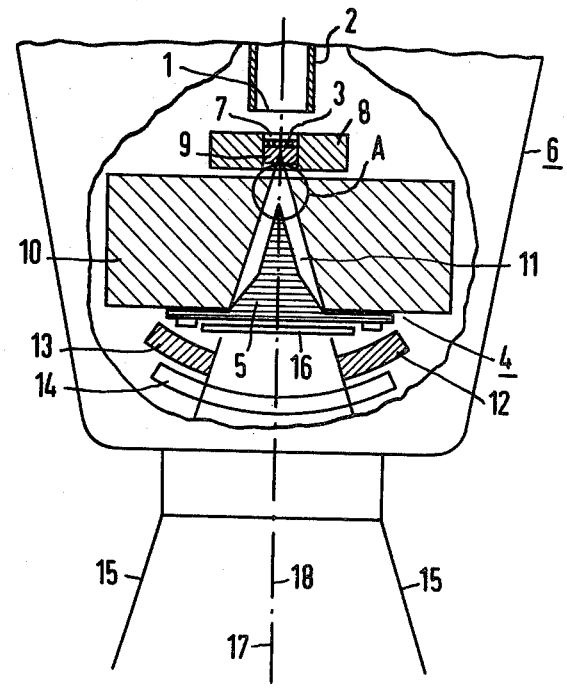
FIG. 1 is a diagrammatic illustration of the partially opened-up beam defining system of an electron accelerator.

FIG. 1 affords a visual recognition of the relative positions of exit window 1 of a vacuum tube 2, of the target 3, collimator 4, and a compensating member 5, in a partially opened-up beam defining system 6 of an electron accelerator. Target 3 is arranged in the radiation direction directly behind exit window 1 of vacuum tube 2. It is mounted in a bore 7 of a carrying plate 8. Disposed in said bore 7 there is an absorption member 9, arranged in the radiation direction directly behind target 3, for the remaining electrons not absorbed in the target. Collimator 4 is disposed in the radiation direction directly behind carrying plate 8 of target 3. Said collimator 4 comprises a thick-walled collimator shielding block 10 with a conical passage opening 11 and with adjustable x-ray shielding plates such as 12, 13, 14, which are adjusted relative to the conical passage opening. Conical passage opening 11 of the collimator shielding block 10 limits (or restricts) the maximum x-ray cone 15. Between the conical passage opening 11 of collimator shielding block 10 and the adjustable x-ray shielding plates such as 12, 13, 14, there is arranged an ionization chamber 16 for the purpose of monitoring the issuing radiation. Conical compensating member 5 is mounted on the collimator shielding block 10 such that it projects inwardly into the conical passage opening 11 of the collimator shielding block. It is centered relative to the central ray 17 which generally corresponds to the symmetry axis 18 of collimator 4.

Figure 2:
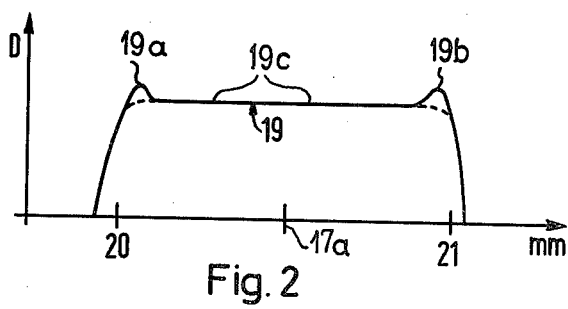
FIG. 2 illustrates a cross-section of the dose characteristic curve of the x-ray cone issuing from an electron accelerator.

The drawn-out (or extended) line 19 of FIG. 2 illustrates (as a function of location expressed in millimeters (mm) in the x-ray cone cross-section) the typical characteristic curve of the dose rate D of the x-ray cone 15 behind compensating member 5. Whereas the dose rate is completely compensated for a good tissue depth (for example, 10 cm), at a lesser tissue depth (for example, 3 cm) it strongly increases in the direction of the edge of the x-ray cone as indicated at 19a and 19b in FIG. 2. For comparison purposes, the margins of the collimated (or defined) region are indicated by two short lines or reference marks 20 and 21 (the central ray location being indicated at 17a). For reasons of radiation therapy, as rectangular a characteristic as possible of the dose rate curve 19 is desirable for all tissue depths in medical technology. Hitherto, the excessive increase in the dose rate in the internal marginal region occurred in the case of all electron accelerators and could, at best, be slightly modified through strong collimation (or defining) of x-ray cone 15 and through filtering, which measures were, however, connected with losses in intensity.

Figure 3:
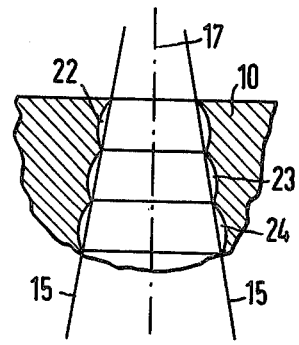
FIG. 3 is an enlarged illustration of the flanks (or defining surfaces) of the collimator in region "A" of FIG. 1.

On the basis of the enlarged illustration of the section of the inner wall surface of collimator shielding block 10 of collimator 4, marked in FIG. 1 by circle A, FIG. 3 shows a sample embodiment of the inventive roughening-up of this wall surface. The wall surface of collimator shielding block 10 is roughened-up by means of rounded grooves 22, 23, 24. From a production engineering standpoint, rounded grooves such as this can be more readily manufactured than stepped grooves. In addition, the path lengths (or distances) in the material are relatively great for weakly scattered rays. The frontal faces of the x-ray shielding plates such as 12, 13, 14, limiting the x-ray cone, can be roughened-up in the same manner as the interior wall surfaces of collimator shielding block 10 of collimator 4.

Figure 4:
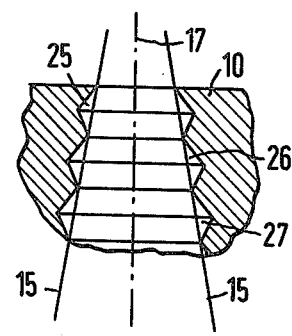
FIG. 4 illustrates a variant embodiment of the flanks (or defining surfaces) of the collimator.
Figure 5:
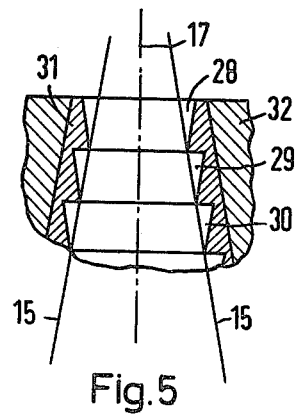
FIG. 5 illustrates another embodiment with stepped flanks.

The sample embodiments of FIGS. 4 and 5 illustrate stepped forms of roughening-up of the interior wall surfaces limiting the x-ray cone. The step-shaped grooves 25, 26, 27, of FIG. 4, yield better results and are also simpler to manufacture than the step-shaped grooves 28, 29, 30, according to FIG. 5. The step-shaped grooves of FIG. 5 are admitted into a sleeve (or bushing) 31 which is inserted into collimator shielding block 32. Sleeve (or bushing) 31 consists of a material of a low atomic number, such as, for example, Fe, Cu, or Al, whose atomic number is less than that of the material of collimator shielding block 32. Accordingly, the forward scattering is even more pronounced in this material. Particularly favorable results can be expected by combining a sleeve (or bushing) consisting of a material having a low atomic number with grooves such as those illustrated in FIGS. 3 and 4.

The x-ray bremsstrahlung is produced by decelerating the electrons in target 3 which have been accelerated in the electron accelerator. This x-ray bremsstrahlung has a conical intensity characteristic. Its intensity maximum coincides with the direction of the original electron beam. The compensating member 5 installed in collimator 4 is precisely adapted with regard to its absorption value to the intensity characteristic of the x-radiation issuing from the target. Accordingly, the dose rate of x-ray cone 15, with the exception of the marginal region, is compensated by the compensating member over the radiation cross-section for all tissue depths as indicated at 19c in FIG. 2. On the interior side of the marginal region of the x-ray cone, the dose rate is normally excessively increased over an annular area of the cone cross section at a low tissue depth, as the drawn-out (or extended) curve 19 of FIG. 2 illustrates at 19a and 19b. This excessive increase is produced by scattering of the x-radiation, which enters at a grazing incidence relative to the inner limiting surfaces of collimator 4, at the atomic lattice of these wall surfaces. Due to the grooves 22, 23, 24, disposed transversely to the radiation direction, at the conical passage opening 11 of collimator shielding block 10, as well as at the frontal surfaces of x-ray shielding plates 13, 14, 15, a large portion of the scatter locations is displaced to the depth of the wall material. The intensity of the scattered radiation component, to which the excessive increase in the dose rate in the marginal region of the x-ray cone at a minimal (or low) tissue depth is attributed, is thus clearly reduced. Even in the case of the stepped grooves of the sample embodiment of FIG. 4, the scattered radiation fraction is reduced because it is strongly absorbed by the edges of the grooves. However, the excessive marginal increase cannot be completely avoided even in the case of stepped grooves, because a scattering of the x-rays in the margins (or borders) of the grooves is itself unavoidable and these radiation components are not completely absorbed in the grooves.

It is entirely possible to provide the grooves with a slight pitch in the manner of a screw thread. A minimal pitch of this type, such as is conventional in the case of screw threads could result in advantages of a production-engineering nature.

The grooves 22-30 are preferably not wider than about 5 mm, the width dimension being generally parallel to the radiation direction of central ray 17.

It will be apparent that many modifications and variations may be effected without departing from the scope of the novel concepts and teachings of the present invention.

We claim as our invention:

1. In an electron accelerator including a target exposed to the electron beam for the purpose of producing x-ray bremsstrahlung, a collimator assembly for providing a compensated dose characteristic over the central region of the cross section of the transmitted x-ray cone, wherein the improvement comprises said collimator assembly having inner wall surfaces at the margin of the x-ray cone which are roughened-up in a direction transverse to the radiation for providing a dose rate at the margin of the transmitted x-ray cone which is relatively uniform and matched to the dose rate at the central region of the transmitted cone, said inner wall surfaces being grooved such that a major portion of the grooved wall is formed by groove portions with a width in the radiation direction of not greater than five millimeters.

2. An electron accelerator according to claim 1, characterized in that the collimator assembly comprises a collimator (4) having said inner wall surfaces at the margin of the x-ray cone and that for providing a dose rate at the margin of the transmitted x-ray cone which is relatively uniform and matched to the dose rate at the central region of the transmitted cone, semicircular-shaped grooves (22, 23, 24) are present in the inner wall surfaces of the collimator (4) in a direction transverse to the radiation direction.

3. An electron accelerator according to claim 1, characterized in that the collimator assembly comprises a collimator (4) having said inner wall surfaces at the margin of the x-ray cone and that for providing a dose rate at the margin of the transmitted x-ray cone which is relatively uniform and matched to the dose rate at the central region of the transmitted cone, stepped grooves (25, 26, 27; 28, 29, 30) are present at the inner wall surfaces of the collimator (4) in a direction transverse to the radiation direction.

4. An electron accelerator according to claim 1, characterized in that the collimator assembly comprises a collimator (4) having said inner wall surfaces at the margin of the x-ray cone and having x-ray shielding plates, and characterized in that the material of the wall surfaces of the collimator (4) consists of a layer (31) corresponding substantially to the roughness depth, said layer comprising a material having a lower atomic number than the material of the x-ray shielding plates.

5. An x-ray collimator assembly comprising a collimator providing a conical passageway for the transmission of an x-ray cone and a conical compensating member centered relative to the central axis of the conical passageway such that the transmitted dose rate behind the conical compensating member is essentially constant over the central region of the transmitted x-ray cone, wherein the improvement comprises the provision of inner wall surfaces defining a conical passageway for the x-ray cone, said inner wall surfaces being grooved to provide axially spaced relatively narrow annular ridge portions each conforming to the perimeter of the conical passageway and relatively wide annular intermediate wall portions providing groove regions such that the annular intermediate wall portions extend outwardly and are clear of the perimeter of the conical passageway, each groove region having a width dimension as measured along the conical passageway which greatly exceeds the width of the annular ridge portions but is not greater than about five millimeters and said grooved inner wall surfaces serving to provide an essentially uniform dose rate at the margin of the x-ray cone matched with the dose rate at the central portion of the transmitted x-ray cone.

6. The collimator assembly of claim 5 further characterized in the ridge portions having a slight pitch in the radiation direction and being connected in the manner of a screw thread.

* * * * *